(12) United States Patent
Güntert et al.

(10) Patent No.: US 6,392,054 B1
(45) Date of Patent: May 21, 2002

(54) 4-ALKANOYL-3-THIAZOLINES AND THEIR USE AS ODORANTS AND FLAVORINGS

(75) Inventors: Matthias Güntert, Ridgewood, NJ (US); Stefan Lambrecht, Holzminden (DE); Wolfgang Engel, Neufahrn (DE); Peter Schieberle, Freising (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/611,164

(22) Filed: Jul. 6, 2000

(30) Foreign Application Priority Data

Jul. 12, 1999 (DE) .......................... 199 32 494

(51) Int. Cl.⁷ ............................ C07D 277/10
(52) U.S. Cl. .................. 548/200; 512/10; 426/535
(58) Field of Search .................. 548/200; 512/10; 426/535

(56) References Cited

U.S. PATENT DOCUMENTS

| 3,778,518 A | 12/1973 | Copier et al. ............. 426/175 |
| 3,816,445 A | 6/1974 | Dubs et al. .............. 260/306.7 |
| 3,876,652 A | * | 4/1975 | Pittet ................ 260/302 |

OTHER PUBLICATIONS

Helvetica Chimica Acta, (month unavailable) 1946, vol. 29(1), pp. 95–101, P. Ruggli et al, "Über die Addition von Benzol an symm. Dibrom–diacetyl".

\* cited by examiner

*Primary Examiner*—Robert Gerstl
(74) *Attorney, Agent, or Firm*—Joseph C. Gil; Noland J. Cheung

(57) ABSTRACT

The present invention provides for novel 3-thiazolines comprising the formula

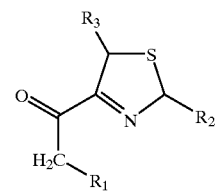

where $R_1$, $R_2$ and $R_3$ are identical or different and denote hydrogen or a lower alkyl, wherein said lower alkyl denotes an unbranched or branched hydrocarbon having 1 to 3 carbon atoms. These novel 3-thiazolines can be used as odorants and flavorings having an olfactory impression.

6 Claims, No Drawings

4-ALKANOYL-3-THIAZOLINES AND THEIR USE AS ODORANTS AND FLAVORINGS

FIELD OF THE INVENTION

The invention relates to novel substituted 3-thiazolines (isothiazolines), processes for their preparation and their use as a flavoring for foods and drinks.

BACKGROUND OF THE INVENTION

In the flavor industry, there is still a strong demand for compounds which give foods and drinks an olfactory impression such as that formed in the thermal treatment during the cooking, baking and roasting treatment of foods. The resultant aromatizing compounds have especially roasted flavor notes. Compounds of this type have hitherto been only scarcely available for industrial use.

The most important reaction which proceeds during the thermal treatment of foods is the reaction between reducing sugars and amino acids, which is termed the Maillard reaction. During this Maillard reaction, flavorings, particularly, heterocyclic substances, are formed. These compounds contain one or more heteroatoms, such as sulphur, nitrogen and oxygen, various side chains and are aromatic or partially hydrogenated.

In the 2-thiazoline class of substances, especially 2-acetyl-2-thiazoline is a known and industrially used flavoring which is used, owing to its flavor properties, in particular, where roasted flavor properties are desired. Thus, 2-acetyl-2-thiazoline is used, for example, for chicken flavors, where it imparts the typical roasted flavor. The threshold value for this 2-thiazoline is reported in the literature at 0.016 to 0.022 ng/l in air (M. Rychlik, P. Schieberle, W. Grosch, Compilation of Odor Thresholds, Odor Qualities and Retention Indices of Key Food Odorants, Deutsche Forschungsanstalt für Lebensmittelchemie und Institut fur Lebensmittelchemie der Technischen Universität Muinchen, Garching, 1998). The threshold value is taken to mean the lowest concentration at which a compound can be detected by sensory means.

SUMMARY OF THE INVENTION

The present invention provides for a 4-alkanoyl-3-thiazolines of the formula

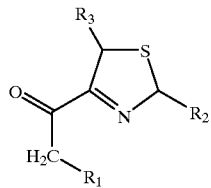

where $R_1$, $R_2$ and $R_3$ are identical or different and denote hydrogen or a lower alkyl for use in a flavoring and/or odorant composition.

DETAILED DESCRIPTION OF THE INVENTION

A lower alkyl denotes an unbranched or branched hydrocarbon having 1 to 3, more preferably 1 or 2, carbon atoms.

The thiazolines of the invention, in particular, 4-acetyl-3-thiazoline, surprisingly have very low threshold values. For example, the 4-acetyl-3-thiazoline ($R_1, R_2, R_3$=H) of the present invention has a threshold value which is 0.005 ng/l in air. This threshold value is, thus, markedly lower than the case for 2-acetyl-2-thiazoline. The compound 4-acetyl-3-thiazoline is, thus, one of the most aroma-intensive compounds.

4-Acetyl-3-thiazoline was identified in a reaction mixture of fructose as the amino acid 4-carboxy-3-thiazolidine (Example 1).

The compound was identified by fractionating the extract from the reaction mixture by multi-dimensional gas chromatography and subsequent mass-spectrometric analysis. 4-Acetyl-3-thiazoline was unambiguously identified by comparison with the analytical data of an authentic sample.

In addition, systematic experiments were also carried out using a cbromatographic method which is termed gaschromatography-olfactometry (GC-O). In this method, the compounds separated during the chromatographic process are sniffed individually using the nose at the end of the capillary column.

Using these methods, the olfactory and gustatory qualities of 4-acetyl-3-thiazoline were determined.

4-Acetyl-3-thiazoline smells and tastes like popcorn and bread crust and has intensely roasted aroma properties.

The structure of the thiazolines of the present invention was demonstrated by comparison with synthesized 4-acetyl-3-thiazoline. 4-Acetyl-3-thiazoline can be prepared starting from diacetyl. Diacetyl is first brominated. The resultant bromodiacetyl is converted by sodium hydrogen sulphide into 1-mercaptodiacetyl. After reaction with formaldehyde solution and ammonia solution and also chromatographic purification, 4-acetyl-3-thiazoline is obtained (Example 2).

The compounds of the invention, because of their excellent organoleptic character, are particularly suitable as odorants and flavorings for use in flavoring compositions and reaction flavors. It is particularly surprising that the 4-acetyl-3-thiazoline imparts to the compositions a highly intense popcorn-like roasted note at extremely low concentrations.

In flavor compositions, the amount of the inventive compound used is preferably between 0.0005 and 1% by weight, in particular between 0.001 and 0.5% by weight, based on the total composition. Flavor compositions of this type can be used in the entire food and drink sector. In particular, they are suitable for aromatizing snacks, soups, sauces, instant meals, fat compositions, bakery products, yogurt, ice cream and confectionery. The dosage of flavor compositions of this type is preferably 0.005 to 2% by weight, and more preferably between 0.01 and 1% by weight, based on the final food or drink.

The flavors can be used in a liquid form, a spray-dried form or an encapsulated form. Whereas, in liquid form, they are used in a solvent which is customary in practice, such as ethanol, propylene glycol, vegetable oil triglycerides or triacetin. The dry flavors are produced by spray-drying or by encapsulation according to one of the processes which are conventional in the flavor industry. These are, in particular, extrusion and spray granulation.

The invention is further illustrated but is not intended to be limited by the following examples in which all parts and percentages are by weight unless otherwise specified.

EXAMPLES

Example 1

Model Reaction Fructose and 4-carboxy-3-thiazolidine 1.8 g of fructose and 0.44 g of 4-carboxy-3-thiazolidine were dissolved in 2.1 g of water and ground with 19.1 g of silica gel. This mixture was heated for 10 min. at 150° C. on an aluminum block under the air atmosphere. After cooling, the mixture was extracted with diethyl ether, the organic phase was washed with sodium hydrogen carbonate solution and with sodium chloride solution, dried over sodium sulphate and concentrated.

The reaction mixture was fractionated by column chromatography on silica gel. The individual fractions were sniffed on the sniffing gas chromatograph, separated by multi-dimensional gas chromatography and then studied by GC/MS. 4-Acetyl-3-thiazoline was unambiguously identified by comparison with the analytical data of an authentic sample.

Example 2

Preparation of 4-acetyl-3-thiazoline 10 mmol of (x-bromocarbonyl compound (prepared by bromination of the corresponding ox-dicarbonyl compound as reported by P. Ruggli, M. Herzog, J. Wegmann, H. Dahn, Helv. Chim. Acta, 1946, 29(1), 95–101 using half the amount of bromine) are added dropwise at 0° C. to a solution of 30 mmol of sodium hydrogen sulfide in 20 ml of 5% sodium hydroxide solution. The mixture is then heated to room temperature and stirred for 1 hour. It is then acidified to pH 3 with 20% citric acid and the mercaptodiketo compound is extracted with ether.

This ether phase is admixed with 10 mmol of aldehyde (formaldehyde as aqueous, 35% solution) and 10 mmol of ammonia solution (aqueous, 25%). The mixture is stirred at room temperature and the course of the reaction is followed by GC/MS. After 1 to 10 hours, the ether phase is concentrated and the mixture is purified by column chromatography using pentane-ether gradients on silica gel. Pure 4-alkanoyl-3-thiazolines are obtained in yields of 5 to 20%.

Mass spectrum of 4-aceltyl-3-thiazoline

TABLE 1

| m/z | Intensity % |
| --- | --- |
| 41 | 15 |
| 42 | 19 |
| 43 | 91 |
| 45 | 29 |
| 46 | 19 |
| 59 | 19 |
| 60 | 19 |
| 86 | 20 |
| 128 | 100 |
| 129 | 66 |

Example 3

Preparation of a Roasted Flavor

The following are mixed (all figures in g):

TABLE 2

| | |
| --- | --- |
| 3-Methylthiopropanal (1% in vegetable oil triglycerides) | 1.0 |
| 2,3-Diethyl-5-methylpyrazine | 1.0 |
| Isoamyl caprylate | 1.0 |
| Diacetyl (10% in triacetin) | 2.0 |
| 2-Methylbutyric acid | 5.0 |
| Isoamyl alcohol | 10.0 |
| Delta-dodecalactone | 10.0 |
| 2-Phenylethanol | 15.0 |

TABLE 2-continued

| | |
| --- | --- |
| 2-Methylbutanal | 20.0 |
| Caprylic acid (10% in triacetin) | 25.0 |
| Dimethyloxyfurone (1% in propylene glycol) | 100.0 |
| 2,5-Dimethyl-4-hydroxy-3(2H)-furanone (15% in propylene glycol) | 500.0 |
| Vegetable oil triglycerides | 9310.0 |
| Total | 10000.0 |

If 0.1 to 0.5 of the solvent vegetable oil triglycerides was replaced by 0.1 to 0.5 g of 4-acetyl-3-thiazoline, the flavor became markedly more typical of popcorn and bread crust.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. 4-Alkanoyl-3-thiazolines comprising the formula

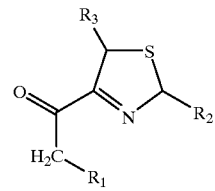

where $R_1$, $R_2$ and $R_3$ are identical or different and denote hydrogen or a lower alkyl, wherein said lower alkyl denotes an unbranched or branched hydrocarbon having 1 to 3 carbon atoms.

2. 4-Alkanoyl-3-thiazolines according to claim 1, in which $R_1$, $R_2$ and $R_3$ are identical or different and denote hydrogen, methyl or ethyl.

3. 4-Alkanoyl-3-thiazolines according to claim 1, wherein said 4-alkanoyl-3-thiazoline is 4-acetyl-3-thiazoline.

4. Flavoring and odorant compositions comprising thiazolines of the formula

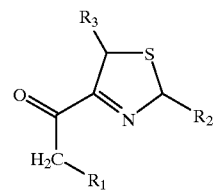

where $R_1$, $R_2$ and $R_3$ are identical or different and denote hydrogen or a lower alkyl, wherein said lower alkyl denotes an unbranched or branched hydrocarbon having 1 to 3 carbon atoms.

5. Flavoring and odorant composition according to claim 4, wherein $R_1$, $R_2$ and $R_3$ are identical or different and denote hydrogen, methyl or ethyl.

6. Flavoring and odorant composition according to claim 4, wherein said 4-alkanoyl-3-thiazoline is 4-acetyl-3-thiazoline.

* * * * *